United States Patent
Wallworth et al.

[11] Patent Number: 5,807,747
[45] Date of Patent: Sep. 15, 1998

[54] METHOD AND APPARATUS FOR DETERMINATION OF GLYCOSYLATED PROTEIN

[75] Inventors: Denise Maria Wallworth, Congleton; Bryan Green, Coventry, both of England

[73] Assignee: Clinical Innovations Limited, Coventry, England

[21] Appl. No.: 697,176

[22] Filed: Aug. 20, 1996

Related U.S. Application Data

[63] Continuation of Ser. No. 420,323, Apr. 11, 1995, abandoned, which is a continuation of Ser. No. 169,721, Dec. 17, 1993, abandoned, which is a continuation of Ser. No. 776,332, filed as PCT/GB90/00907, Jun. 12, 1990 published as WO90/15995, Dec. 27, 1990, abandoned.

[30] Foreign Application Priority Data

Jun. 13, 1989 [GB] United Kingdom ............... 8913586

[51] Int. Cl.$^6$ .................................................. G01N 33/72
[52] U.S. Cl. .............................. 436/67; 436/15; 436/63; 436/86; 436/66; 436/164; 436/165; 436/169; 436/172; 422/56; 422/58
[58] Field of Search ................. 422/56, 58; 436/15, 436/63, 86, 67, 164, 165, 169, 172, 66

[56] References Cited

U.S. PATENT DOCUMENTS

| | | | |
|---|---|---|---|
| 4,200,435 | 4/1980 | Stroupe et al. | 436/67 |
| 4,238,196 | 12/1980 | Acuff et al. | 23/230 B |
| 4,255,385 | 3/1981 | Stroupe et al. | 436/67 X |
| 4,268,270 | 5/1981 | Gabbay et al. | 422/58 X |
| 4,269,605 | 5/1981 | Dean et al. | 436/67 |
| 4,334,879 | 6/1982 | Fujimori | 436/174 |
| 4,349,352 | 9/1982 | Manning et al. | 436/67 |
| 4,371,374 | 2/1983 | Cerami et al. | 422/56 X |
| 4,407,961 | 10/1983 | Sanders | 436/67 |
| 4,409,335 | 10/1983 | Hanamoto et al. | 436/67 |
| 4,436,820 | 3/1984 | Reiter | 436/67 |
| 4,465,774 | 8/1984 | Huang et al. | 436/15 |
| 4,635,488 | 1/1987 | Kremer | 422/58 |
| 4,649,122 | 3/1987 | Lee | 436/67 X |
| 4,658,022 | 4/1987 | Knowles et al. | 436/86 X |
| 4,695,552 | 9/1987 | Schmitt et al. | 436/66 |
| 4,737,544 | 4/1988 | McCain et al. | 424/409 X |
| 4,806,468 | 2/1989 | Wagner et al. | 436/67 X |
| 4,810,391 | 3/1989 | Bruegger | 210/656 |
| 4,818,710 | 4/1989 | Sutherland et al. | 436/165 X |
| 4,820,636 | 4/1989 | Hill et al. | 436/67 X |
| 4,861,728 | 8/1989 | Wagner | 436/67 X |
| 4,876,205 | 10/1989 | Green et al. | 436/66 |
| 4,980,058 | 12/1990 | Bruegger | 210/198.2 |
| 4,990,075 | 2/1991 | Wogoman | 422/58 |
| 5,094,819 | 3/1992 | Yager et al. | 422/58 X |
| 5,106,761 | 4/1992 | Kuniyuki | 422/58 X |
| 5,110,745 | 5/1992 | Kricka et al. | 436/67 X |
| 5,198,193 | 3/1993 | Bonce et al. | 422/100 |
| 5,242,842 | 9/1993 | Sundrehagen | 436/67 X |
| 5,256,372 | 10/1993 | Brooks | 422/58 |
| 5,292,663 | 3/1994 | Yamazaki et al. | 436/67 |

FOREIGN PATENT DOCUMENTS

| | | | |
|---|---|---|---|
| 1167278 | 5/1984 | Canada | 436/67 |
| 2206411 | 1/1989 | United Kingdom | 436/67 |
| 8201804 | 5/1982 | WIPO | 436/67 |

*Primary Examiner*—Harold Y. Pyon
*Assistant Examiner*—Sharidan Carrillo
*Attorney, Agent, or Firm*—Salter & Michaelson

[57] ABSTRACT

A method of determining the glycosylated fraction of a protein in a sample includes the steps of examining the sample to determine the total quantity of protein in the sample (READ 1), removing the glycosylated fraction of the protein, and then reexamining the sample to measure the glycosylated fraction of the protein (READ 2). The glycosylated fraction of the protein may then be calculated by the formula (READ 1–READ 2)/READ ×100. The glycosylated fraction of the protein is removed by inserting a cartridge containing a binder into the sample, or by urging the sample through a cartridge containing a binder. Both of the cartridge assemblies preferably include a flow through body, a support material disposed in the body, and a binder material attached to the support wherein the binder has an affinity for the glycosylated fraction of the protein.

10 Claims, 1 Drawing Sheet

METHOD AND APPARATUS FOR DETERMINATION OF GLYCOSYLATED PROTEIN

This is a continuation of application Ser. No. 08/420,323, filed Apr. 11, 1995, now abandoned, which is a continuation of application Ser. No. 08/169,721, filed Dec. 17, 1993, now abandoned, which is a continuation of application Ser. No. 07/776,332, filed as PCT/GB90/00907, Jun. 12, 1990 published as WO90/15995, Dec. 27, 1990, now abandoned.

TECHNICAL FIELD

This invention relates to a method of determining the glycosylated protein level of a sample and an apparatus for use in the method and is particularly, but not exclusively, relevant to determining the level of glycosylated hemoglobin and other glycosylated proteins in biological fluids.

BACKGROUND ART

Known methods of determining the concentration of glucose in blood at a particular instant include a range of stick tests and meters which are often used for routine assessment by a patient, for example a diabetic.

However, the results provided by such methods and apparatus cannot be relied upon to give an accurate retro-respective indication of the long term control of blood glucose concentration.

When the patient visits his doctor a sample of blood is taken from the patient which is forwarded to a laboratory for analysis.

Laboratory analysis involves the determination of glycosylated hemoglobin or other glycosylated protein which provides a reliable retrorespective indication of the long term averaged glucose concentration of the blood. Glycosylated hemoglobin results are expressed ratiometrically as a percentage of the total hemoglobin level.

Techniques which are currently available for laboratory analysis include affinity gel chromatography and ion exchange liquid chromatography (IELC).

The time taken to analyze a blood sample using affinity chromatography is in the order of two to three hours.

The IELC apparatus is bulky and expensive. Also the time taken to prepare a sample prior to running a chromatogram using IELC is in the order of forty minutes. The time taken to run the chromatogram is in the order of seven minutes.

All of these methods rely upon the separation of glycosylated hemoglobin from non-glycosylated hemoglobin and its subsequent direct measurement as a discrete analyte by techniques involving multiple reagent reactions. None of these methods and apparatus is suitable for use by the medical practitioner in a clinic.

In practice the results of these tests do not return from the laboratory for several days and the doctor cannot inform the patient of the results of this test and advise an appropriate change of diet and/or therapy if required until these results have arrived.

The present invention has been made from a consideration of this problem.

According to a first aspect of the invention there is provided a method of determining the glycosylated protein level of a sample comprising bringing a quantity of sample into contact with a material having an affinity for the glycosylated protein whose level is to be determined or an affinity for substances in the sample other than the glycosylated protein whose level is to be determined, and optically, electrochemically or enthalpiometrically examining the sample and/or optically, electrochemically, or enthalpiometrically examining the said material characterised in that the sample and/or the material is examined before contact with the material and/or sample respectively and in that the sample and/or material is examined after contact with the material and/or sample respectively to obtain a substantially immediate reading or readings indicative of the glycosylated protein level in the sample.

According to a second aspect of the present invention there is provided an apparatus for determining the glycosylated protein level of a sample, comprising a support for a material having an affinity for the glycosylated protein whose level is to be determined or an affinity for substances in the sample other than the glycosylated protein whose level is to be determined, means for bringing the sample into contact with said material characterised by means for optically, electrochemically or enthalpiometrically examining the sample and/or optically, electrochemically, or enthalpiometrically examining said material before contact of the sample with the material and for optically, electrochemically or enthalpiometrically examining the sample and/or optically, electrochemically, or enthalpiometrically examining said material after contact of the sample with the material The material having an affinity for the glycosylated protein is preferably phenylboronic acid or a derivative thereof.

The said material is preferably bonded to a suitable support such as a hydroxyethyl methacrylate copolymer in microparticulate form or a nylon membrane. In a further alternative the said material may be present as a film.

The level of any glycosylated protein may be determined such as glycosylated hemoglobin, glycosylated albumin or glycosylated serum protein.

The sample is preferably taken using a wick which is chemically treated with a lysing agent such as syperonic N. At least one indication is provided on the wick in order to indicate the correct sample size. This indication is provided part way up the wick in order that the wick has additional capacity to absorb further sample. At least a part of the wick which is located above the wick may be covered preferably by a transparent or translucent cover, such that when the wick is brought into contact with a reaction mixture so as to transfer the sample into the reaction mixture the amount of dissolution from that covered part of the wick is reduced. The diameter of the top of the wick is preferably less than the diameter of the body of the wick. The wick is preferably made from a cellulose acetate material or a derivative thereof. This cellulose acetate material is similar to that conventionally used in cigarette filter tips.

Preferably the sample is diluted in buffer solution prior to administering the sample to the said material.

Preferably the said material is maintained in a container or cartridge through the wall of which one or more apertures pass so as to allow the sample to gain access to the said material.

The amount of sample used is preferably small and in any event much smaller than samples required for known methods.

In a preferred embodiment of the invention the sample may be added to a container containing said material such as coupled phenylboronic acid. Monitoring means such as a photometer may be used to optically determine the total quantity of a certain protein prior to adding the sample to the cartridge (READ 1). Monitoring means may be used to optically determine the total quantity of the protein less the total quantity of any glycosylated protein (READ 2) after the sample has passed through the cartridge.

The percentage of that glycosylated protein (% GP) in the sample may then be derived from the following equation:

$$\% GP = \frac{READ\ 1 - READ\ 2}{READ\ 1} \times 100 \qquad \text{Equation A}$$

Alternatively the sample may be held in a container to which a cartridge of the said material such as coupled phenylboronic acid is added. A monitoring means such as a photometer may be used to determine the total quantity of a certain protein (% GP) prior to adding the cartridge to the sample (READ 1). A monitoring means may then be used to optically determine the total quantity of protein in the sample less the total quantity of glycosylated protein (READ 2) once the cartridge has been added to the sample.

The percentage of the glycosylated protein (% GP) in the sample may then be determined using the above Equation A.

BRIEF DESCRIPTION OF THE DRAWINGS

In order that the invention may be more readily understood specific embodiments thereof will now be described by way of example only with reference to the accompanying drawings in which.

BEST MODE FOR CARRYING OUT THE INVENTION

Figure 1:
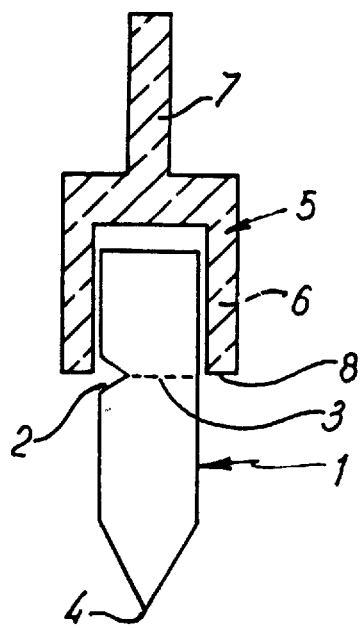
FIG. 1 is a preferred form of metering device for taking a blood sample the glycosylated protein level of which is to be determined.

Referring to FIG. 1 there is shown a wick 1 comprising a pad made from a cellulose acetate based material. This material allows in the order of 60–70% dissolution of blood samples. An indentation 2 and marking 3 are provided part way up the wick 1 so as to provide an indication to the user of the required quantity of sample to be taken up by the wick 1. It is noted that the upper part of the wick 1 is not saturated by the sample when the required size of sample has been taken.

The wick 1 is chemically treated with a lysing agent such as syperonic N. This may be achieved by bringing the wick 1 into contact with the lysing agent until the wick 1 is saturated with lysing agent. The wick 1 is subsequently allowed to dry.

The tip 4 of the wick 1 is seen to have a more narrow diameter than the body of the wick 1. Alternatively the diameter of the wick 1 may be uniform.

The top of the wick 1 is located in a cap 5. The cap 5 comprises a cover 6 and a handle 7. The height of the cover 5 is such that when in position the base 8 of the cover 5 is substantially adjacent indications 2, 3. The cover 5 is preferably made from transparent or translucent plastics material in order that the upper part of the wick 1 can be seen through the cover 5.

When in use the tip 4 of the wick 1 is brought into contact with the blood causing blood to rise up the wick by capillary action. As the blood rises up the wick 1 the lysing agent located on the wick 1 causes rupture of the erythrocyte membrane allowing release of the hemoglobin from the cells.

As the blood level reaches the indications 2, 3 the wick 1 is removed from the sample. The resultant residual amount of blood located at the tip 4 of the wick 1 causes the blood level to rise above the indications 2, 3 resulting in an oversampling. This will lead to a small percentage error. However more importantly as the lysing agent is present along the entire length of the wick substantially no non-lysed erythrocytes will be present on the wick. This is a very important consideration with this type of analysis.

The sample is transferred from the wick 1 by shaking the wick 1 in buffer solution causing dissolution of the sample. However as the cap 5 covers the upper part of the wick 1 dissolution of any sample above the indications 2, 3 is substantially prevented.

Figure 2:
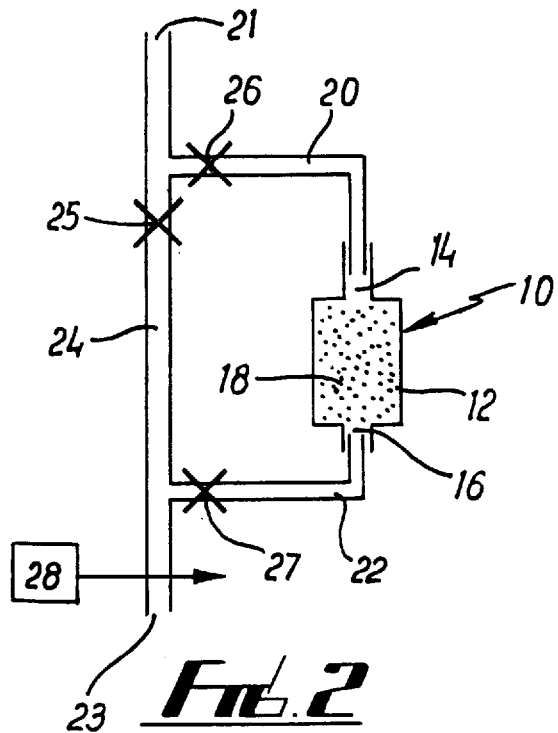
FIG. 2 is a side elevation of one embodiment of the apparatus of the present invention.

Referring to Fig. 2 an apparatus 10 for determining the glycosylated protein level of the sample such as in this example the determination of the glycosylated hemoglobin level of blood comprises a cartridge 12 with an inlet 14 and outlet 16. The cartridge contains coupled phenylboronic acid adsorbed to a support 18.

One end of an entrance tube 20 is received in the inlet 14 and the other end of the entrance tube 20 is connected to a bypass tube 24. One end of a waste tube 22 is received in the exit 16 and the other end of the waste tube 22 is connected to the bypass tube 24.

A tap 25 is provided in the bypass tube 24 intermediate the mouths of the entrance tube 20 and waste tube 22.

A further tap 26 is provided at the mouth of the entrance tube 20 and a tap 27 is provided at the exit of the waste tube 22. In use, for example, a blood sample is diluted in a buffer solution and is added to one end 21 of the bypass tube 24. With taps 26 and 27 closed and tap 25 open this mixture is urged down the bypass tube 24. A photometer 28 is used to determine the total level of hemoglobin in the sample (READ 1) at the exit 23 of the bypass tube 24.

Subsequently tap 25 is closed and taps 26, 27 are opened and the mixture is urged down the entrance tube 20 and over the phenylboronic acid and its support 18 under pressure by a suitable device which is not illustrated.

As the sample passes over the phenylboronic acid the glycosylated hemoglobin in the blood sample is retained in the cartridge 12.

The remainder of the blood sample passes through the cartridge 12, through the waste pipe 22 and the exit 23 of the bypass tube 24.

The photometer 28 is used to determine the level of hemoglobin in the sample less the content of glycosylated hemoglobin (READ 2). The wavelength of light emitted from the photometer may be varied depending on the material in respect of which the measurements are being taken.

In this example the wavelength of emitted light of the photometer is 414 nm.

The percentage level of glycosylated hemoglobin in the blood sample may be determined using Equation A.

The time taken to take the necessary measurements is in the order of two minutes.

The cartridge device described is cost effective to produce and may be disposed of once used.

Figure 3:
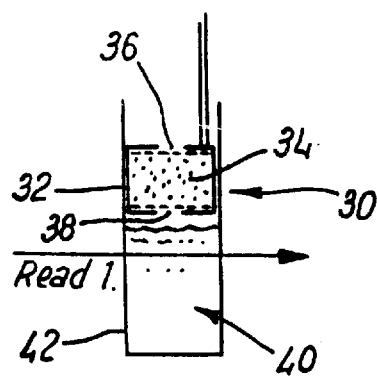
FIG. 3 is a side elevation of a second embodiment of the apparatus of the present invention.
Figure 4:
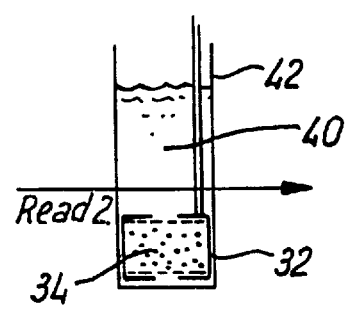
FIG. 4 is a side elevation of the apparatus of Fig.3 in which the said material has been added to the sample.

Referring now to FIGS. 3 and 4 an apparatus 30 for determining the level of glycosylated protein of a sample for example the glycosylated hemoglobin level of a blood sample comprises a cartridge 32 containing phenylboronic acid coupled to a support such as a co-polymer of hydroxyethylmethacrylate 34. The cartridge 32 has two ports 36, 38.

A blood sample 40 diluted in buffer solution is contained in a vessel 42.

In use a monitoring device such as a photometer is used to optically determine the amount of hemoglobin present in the blood sample 40 (READ 1).

Subsequently the cartridge 32 is entirely immersed in the blood sample 40 and buffer as is shown in FIG. 3 such that the blood sample can gain access to coupled phenylboronic acid via the port 38. Glycosylated hemoglobin in the blood sample 40 has an affinity for the phenylbornoic acid contained in the cartridge and is retained in the cartridge.

A second measurement is then taken using suitable monitoring means such as the photometer to optically determine the total amount of hemoglobin in the blood sample less than the amount of glycosylated hemoglobin (READ 2).

The level of glycosylated hemoglobin in the blood sample may be determined using Equation A.

It can be seen from the above described embodiments that the invention provides a quick, cost effective method of monitoring the level of glycosylated proteins in samples of materials such as blood which may easily be carried out in a doctor's surgery.

It is to be understood that the above described embodiments are by way of illustration only and that many modifications and variations can be made within the scope of the invention. For example the level of glycosylated protein in the sample may be determined electrochemically or enthalpiometrically.

We claim:

1. A method of determining a percentage of glycosylated fraction (% GP) of a protein in a sample consisting essentially of:

diluting said sample in a buffer solution thereby forming a buffered sample solution;

conducting a first examination (READ 1) of said buffered sample solution using a measuring means to determine a total quantity of said protein including said glycosylated fraction in said sample;

inserting a cartridge assembly into said buffered sample solution, said cartridge assembly including a support material and a binder attached to said support material, said binder having an affinity for the glycosylated fraction of said protein, said binder binding to and removing the glycosylated fraction of said protein in said buffered sample solution from said buffered sample solution;

conducting a second examination (READ 2) of the buffered sample solution using said measuring means to determine the total quantity of said protein remaining after removal of said glycosylated fraction of said protein;

wherein the glycosylated fraction of said protein is not measured during said second examination;

directly calculating from the total quantities of protein obtained by the first and second examinations the percentage of the glycosylated fraction of the protein in said sample by using the following equation:

$$\% \ GP = \frac{(READ\ 1 - READ\ 2) \times 100}{READ\ 1}.$$

2. The method of claim 1 wherein said buffered sample solution is examined optically.

3. A method of determining a percentage of glycosylated fraction (% GP) of a protein in a sample consisting essentially of:

diluting said sample in a buffer solution thereby forming a buffered sample solution;

urging said buffered sample solution through an examination station;

conducting a first examination (READ 1) of said buffered sample solution using a measuring means while said buffered sample solution is passing through said examination station to determine a total quantity of said protein including said glycosylated fraction in said buffered sample solution, urging said buffered sample solution through a cartridge assembly, said cartridge assembly including a support material and a binder attached to said support material, said binder having an affinity for the glycosylated fraction of said protein, in said buffered sample solution, said binder binding to and removing the glycosylated fraction of said protein from said buffered sample solution when said buffered sample solution is urged therethrough;

urging said buffered sample solution through said examination station a second time;

conducting a second examination (READ 2) of said buffered sample solution using said measuring means while said buffered sample solution is passing through said examination station to determine the total quantity of said protein remaining after removal of said glycosylated fraction wherein the glycosylated fraction of said protein is not measured during said second examination; and directly calculating from the total quantities of protein obtained by the first and second examinations the percentage of the glycosylated fraction of the protein in said sample by using the following equation:

$$\% \ GP = \frac{(READ\ 1 - READ\ 2) \times 100}{READ\ 1}.$$

4. The method of claim 3 wherein said buffered sample solution is examined optically.

5. A system for determining a percentage of glycosylated fraction (% GP) of a protein in a sample consisting essentially of:

a) a metering device for obtaining said sample;

b) a buffered solution for diluting said sample and forming a buffered sample solution;

c) an apparatus for holding said buffered sample solution, said apparatus comprising an entrance tube for receiving said buffered sample solution and a bypass tube, wherein said entrance tube is connected to said bypass tube;

d) a first valve means positioned in said entrance tube for transporting said buffered sample solution through said entrance tube;

e) a measuring means positioned adjacent said entrance tube for measuring a first value (READ 1) representing a total quantity of said protein include said glycosylated fraction as said buffered sample solution is transported through said entrance tube by said first valve means;

f) a cartridge assembly positioned in said bypass tube, said cartridge assembly including a flow through body, a support material disposed in said flow through body, and a binder material imbedded in said support material, said binder material binding to and removing the glycosylated fraction of said protein from said buffered sample solution;

g) a second valve means positioned in said bypass tube for transporting said buffered sample solution from said entrance tube to said cartridge assembly to remove said glycosylated fraction of said protein, said buffered sample solution being measured a second time by said measuring means to determine a second value (READ 2) representing the total quantity of protein remaining in said buffered sample solution after removal of said glycosylated fraction, wherein the percentage of glycosylated fraction of the protein in said buffered sample solution is determined from said first and said second values by the following equation:

$$\% GP = \frac{READ\ 1 - READ\ 2}{READ\ 1} \times 100. \quad \text{Equation A}$$

6. The apparatus of claim 5, wherein said measuring means comprises an optical examining device.

7. The apparatus of claim 5, wherein said binding material comprises phenylboronic acid.

8. The apparatus of claim 5, wherein said support material comprises a hydroxyethyl methacrylate co-polymer in particulate form.

9. The apparatus of claim 5, wherein said support material comprises a nylon membrane.

10. The apparatus of claim 5, wherein said metering device comprises cellulose acetate.

* * * * *